United States Patent [19]  [11] 4,065,465
Denny  [45] Dec. 27, 1977

[54] PROCESS FOR THE PREPARATION OF SUBSTITUTED TRICHLOROACETAMIDINE DERIVATIVES

[75] Inventor: George H. Denny, Lansdale, Pa.

[73] Assignee: Merck & Co., Inc., Rahway, N.J.

[21] Appl. No.: 691,280

[22] Filed: June 1, 1976

[51] Int. Cl.$^2$ ............................................ C07D 209/14
[52] U.S. Cl. ................................ 260/326.15; 560/251
[58] Field of Search .................................... 260/326.15

[56] References Cited
U.S. PATENT DOCUMENTS
2,855,398  10/1958  Voegtli .......................... 260/326.15

OTHER PUBLICATIONS

Gautier et al., The Chemistry of Amidines & Imidates, 1975, John Wiley & Sons, pp. 310–313.
Sandler and Karo, Organic Functional Group Preparations, vol. III, (1972), Academic Press, pp. 217–221.

Primary Examiner—Ethel G. Love
Attorney, Agent, or Firm—David L. Rose; J. Jerome Behan

[57] ABSTRACT

Substituted trichloroacetamidine derivatives are prepared by reacting an appropriately substituted amine with trichloroacetamidine or a trichloroacetimidate. The substituted amines are 3-aminomethyl indole and 2-acetoxy-3-phenoxy propylamine.

3 Claims, No Drawings

PROCESS FOR THE PREPARATION OF SUBSTITUTED TRICHLOROACETAMIDINE DERIVATIVES

SUMMARY OF THE INVENTION

This invention is related to a novel process for the preparation of certain trichloroacetamidine derivatives. Specifically this process is concerned with the reaction of an appropriately substituted amine with trichloroacetamidine or a trichloroacetimidate, preferably a loweralkyl trichloroacetimidate. Thus, it is an object of this invention to describe the process for the reaction of trichloroacetamidine or a trichloroacetimidate with an amine to yield the desired trichloroacetamidine derivatives. Further objects will become apparent from a reading of the following description of the invention.

DESCRIPTION OF THE INVENTION

N-(3-indolylmethyl) trichloroacetamidine and N-(2-acetoxy-3-phenoxypropyl)-trichloroacetamidine are potent cardiotonic agents. A cardiotonic agent stimulates the contractile force of the heart muscle and thus increases the cardiac output. A cardiotonic agent is required for the treatment of congestive heart failure which results when the heart pumps less blood than is required by the metabolic demands of the body. The objective of treatment of congestive heart failure is to restore the balance of supply and demand for blood. This can be achieved through the instant cardiotonic agents which improve myocardial contractility and influence cardiac output to meet the demands of the body.

The above compounds are prepared by reacting trichloroacetamidine or a trichloroacetimidate with an appropriately substituted amine as shown in the following reaction scheme:

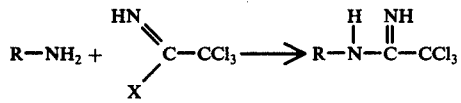

wherein R is 3-indolylmethyl or 2-acetoxy-3-phenoxypropyl; and X is amino or loweralkoxy.

The foregoing reaction is carried out by combining the starting materials at from room temperature to 100° C. for from 30 minutes to 40 hours. It is preferred to employ a solvent for the reaction, however, the choice of solvent is not critical and any solvent capable of dissolving the reactants to any appreciable extent may be employed. Exemplary solvents are hydrocarbons, halogenated hydrocarbons, alcohols, ethers and other solvents such as dimethylsulfoxide, dimethylformamide, hexamethylphosphoramide and the like. Mixtures of solvents may also be employed.

The preferred trichloroacetimidates are methyl and ethyl trichloroacetimidate. The starting materials for this reaction are known in the literature or processes for their preparation are readily available to those skilled in this art.

The initial combination of the reagents may result in an exothermic reaction, thus it may be desirable to combine the reagents in a dropwise fashion over a period of about 5 to 30 minutes. Also the reagents may be combined in the lower temperature ranges, or less to moderate any possible exothermic reaction.

The reaction is preferably carried out at from about room temperature to about 75° C. in which case the reaction is generally complete in from 1 to 24 hours.

Since both starting materials and the product of this invention are basic compounds, it is possible, and may be desirable to employ the acid addition salt of one or both starting materials in the process, or to isolate the product in the form of the acid addition salt. The mineral acid salts such as hydrohalide (hydrochloride), nitrate, sulfate and the like are preferred. They are prepared from the free base, and the free base is liberated therefrom by procedures known to those skilled in the art.

The following examples are provided in order that the process might be more fully understood. The examples should not be construed as limitative of the invention.

EXAMPLE 1

N-(3-indolylmethyl)-trichloroacetamidine

A solution of 5.72 g. (0.033 mole) of methyl trichloroacetimidate in 15 ml. of benzene is added over 15 minutes to a stirred solution of 3.18 g. (0.022 mole) of 3-aminomethylindole in 25 ml. dry dimethylsulfoxide at room temperature. The mixture is stirred for 20 hours at room temperature, concentrated to dryness, and the residue taken up in warm chloroform.

The chloroform solution is washed with 2 portions of water and extracted with 3 portions of dilute hydrochloric acid. The aqueous acid extracts are combined, extracted with 2 portions of chloroform and filtered. The clear aqueous filtrate is made basic with a saturated aqueous solution of sodium bicarbonate and the product extracted into 3 portions of chloroform. The combined chloroform extracts are washed with water, dried over magnesium sulfate, filtered and concentrated to dryness to afford N-(3-indolylmethyl)-trichloroacetamidine, which after crystallization from benzene/hexane has a m.p. of 135.5° to 138.5° C.

EXAMPLE 2

Triethylamine (0.50 g., 5.0 mmoles) is added in small portions over 10 minutes to a well stirred mixture of 1.23 g. (5.0 mmoles) of 2-acetoxy-3-phenoxy-propylamine hydrochloride and 1.61 g. (10 mmoles) of trichloroacetamidine in 5 ml. of dimethylformamide. The reaction mixture is heated at 60° C. for 2 hours, diluted with water and extracted with benzene. The benzene extract is washed with water, dried over magnesium sulfate, filtered and concentrated. The residue is dissolved in benzene and treated with an excess of ethanolic hydrogen chloride. Concentration to dryness affords N-(2-acetoxy-3-phenoxypropyl) trichloroacetamidine hydrochloride with a m.p. of 70° to 77° C.

What is claimed is:

1. A process for the preparation of a compound having the formula:

wherein R is 3-indolylmethyl;
which comprises treating a compound having the formula:

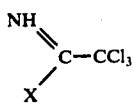
wherein
X is amino or loweralkoxy; with a compound having the formula:
R—NH$_2$
wherein
R is as previously defined, at from room temperature to 100° C for from 30 minutes to 40 hours.
2. The process of claim 1 wherein X is amino, methoxy or ethoxy.
3. The process claim 1 wherein the reaction is carried out at from room temperature to 75° C.
* * * * *